United States Patent
Boyd et al.

(10) Patent No.: US 10,518,113 B2
(45) Date of Patent: Dec. 31, 2019

(54) DENTIFRICE COMPOSITION AND METHOD OF USE

(75) Inventors: Thomas Boyd, Metuchen, NJ (US); Evangelia Arvanitidou, Princeton, NJ (US); Joe Vazquez, Hamilton, NJ (US); Ying Yang, Monmouth Junction, NJ (US); Qing Claire He, Jersey City, NJ (US); Mary Horchos, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 1479 days.

(21) Appl. No.: 13/262,493

(22) PCT Filed: Apr. 2, 2009

(86) PCT No.: PCT/US2009/039319
§ 371 (c)(1),
(2), (4) Date: Sep. 30, 2011

(87) PCT Pub. No.: WO2010/114549
PCT Pub. Date: Oct. 7, 2010

(65) Prior Publication Data
US 2012/0034282 A1    Feb. 9, 2012

(51) Int. Cl.
*A61K 8/25*    (2006.01)
*A61Q 11/00*    (2006.01)

(52) U.S. Cl.
CPC .................. *A61Q 11/00* (2013.01)

(58) Field of Classification Search
CPC ...... A61K 2800/28; A61K 8/25; A61K 8/365; A61K 8/731; A61K 8/732; A61Q 11/00
See application file for complete search history.

(56) References Cited

U.S. PATENT DOCUMENTS

| | | | |
|---|---|---|---|
| 4,391,798 A | 7/1983 | Tavss et al. | |
| 5,149,521 A | 9/1992 | Hirose et al. | |
| 5,496,541 A | 3/1996 | Cutler | |
| 5,700,449 A | 12/1997 | Katayama et al. | |
| 6,274,364 B1 | 8/2001 | Bernard et al. | |
| 6,379,654 B1 | 4/2002 | Gebreselassie et al. | |
| 6,645,509 B1 | 11/2003 | Serre et al. | |
| 6,652,841 B1 | 11/2003 | Brown et al. | |
| 8,673,271 B2 | 3/2014 | Kato et al. | |
| 2002/0156130 A1* | 10/2002 | Melman | 514/557 |
| 2003/0103913 A1* | 6/2003 | Nathoo | 424/53 |
| 2003/0211054 A1 | 11/2003 | Szeles et al. | |
| 2005/0163727 A1* | 7/2005 | Doyle et al. | 424/48 |
| 2006/0188452 A1 | 8/2006 | Rochat | |
| 2006/0210511 A1* | 9/2006 | Stone et al. | 424/70.13 |

FOREIGN PATENT DOCUMENTS

| | | | |
|---|---|---|---|
| EP | 0269966 A1 * | 6/1988 | ........... A61K 8/0225 |
| EP | 0711544 | 5/1996 | |
| GB | 2210264 | 6/1989 | |
| JP | 55-69508 | 5/1980 | |
| JP | 56-073015 | 6/1981 | |
| RU | 2241437 | 12/2004 | |
| RU | 2280435 | 1/2006 | |
| WO | WO 95/034275 | 12/1995 | |
| WO | WO 99/043291 | 9/1999 | |
| WO | WO 01/045660 | 5/2001 | |
| WO | WO 03/061908 | 7/2003 | |
| WO | WO 06/128269 | 12/2006 | |
| WO | WO 07/091856 | 8/2007 | |

OTHER PUBLICATIONS

De Boever et al., 1995, "Assessing the Contribution of Anaerobic Microflora of the Tongue to Oral Malodor," JADA 126(10):1384-1393.
De Boever et al., 1995, "Role of Tongue Surface Characteristics and Tongue Flora in Halitosis," J. Dental Research 74(Suppl. 1):127, Abstract 923.
International Search Report and Written Opinion in International Application No. PCT/US09/039319 dated Apr. 6, 2010.
Yaegaki et al., 2002, "Tongue brushing and mouth rinsing as basic treatment measures for halitosis," International Dental Journal 52(Suppl. 3):192-196.
Database GNPD [online] MINTEL; "Toothpaste," Database accession No. 990958, Oct. 2008.
Du, et al., ed., 2005, "V. Collagen Repair Phase," in: Facial Rejuvenation, p. 225.
Shi et al., 1993, "Salicylic acid," in: Practical Oral Medication Manual, p. 23.
Wang, ed., 2005, "Section 2 Friction Agent Used in Toothpaste," in: Daily Chemicals: Fine Chemical Raw Materials and Intermediate Manual, p. 959.

\* cited by examiner

*Primary Examiner* — Ernst V Arnold

(57) ABSTRACT

An exfoliating dentifrice composition is described that contains a plurality of granules and an orally acceptable vehicle. The granules include at least one polymeric binding agent. The composition includes at least one abrasive agent having an average particle diameter of 0.01 mm to 4 mm. Also included are methods of exfoliating an oral cavity soft tissue by use of the composition.

11 Claims, No Drawings

DENTIFRICE COMPOSITION AND METHOD OF USE

CROSS-REFERENCE TO RELATED APPLICATIONS

The present application is a national stage entry under 35 U.S.C. § 371 of International Patent Application No. PCT/US2009/039319, filed Apr. 2, 2009, the entirety of which is hereby incorporated by reference.

BACKGROUND OF THE INVENTION

The benefits of mechanical exfoliation are well-known in the personal care field for skin and epidermal application. However, patents and literature related to oral care have focused on the negative effects of "sloughing" and extreme increases in desquamation rate. Common dentifrice surfactants have been cited to irritate oral and gastric mucosa and are even thought to contribute to periodontal disease because they allegedly cause chronic inflammation and sloughing of oral mucosa, thus facilitating infection by pathogenic microorganisms.

Chemical exfoliation is well known in the dermal health area and often involves the use of agents that accelerate the rate of desquamation. Alpha or beta hydroxyacids with a pH of 3-4 are known to increase the activity of enzyme process in personal care products but can be too aggressive for oral cavity use. Proteolytic enzymes have also been reported for their utility in reducing oral biofilm, but thus far have not been disclosed for use as a soft tissue exfoliant.

BRIEF SUMMARY OF THE INVENTION

Embodiments of the present invention include a dentifrice composition which will provide positive results from exfoliating the oral mucosa.

An exfoliating dentifrice composition is described that contains a plurality of granules and an orally acceptable vehicle. The granules include at least one polymeric binding agent and the composition includes at least one abrasive agent having an average particle diameter of 0.01 mm to 4 mm. Also included are methods of exfoliating an oral cavity soft tissue by use of the composition.

Systems for exfoliation of the oral cavity soft tissues are described that include compositions as described above and an oral care implement for effectuation of the exfoliating activities.

DETAILED DESCRIPTION OF THE INVENTION

As used throughout, ranges are used as shorthand for describing each and every value that is within the range. Any value within the range can be selected as the terminus of the range.

In some embodiments, an exfoliating dentifrice composition of the present invention includes granules which include a thickening agent and a plasticizer. In some embodiments, a dentifrice composition of the present invention may be applied to the oral cavity of a user to exfoliate or increase desquamation of the oral cavity.

The term "dentifrice" shall include toothpastes, gels, and rinses, alone or in combination. The dentifrice composition may be in any desired form, such as but not limited to deep striped, surface striped, multilayered, or any combination of gel and toothpaste. A carrier for the components of the dentifrice composition may include any orally acceptable vehicle suitable for use in the oral cavity, as described below. The granules of the dentifrice and vehicles for carrying the granules are described below.

In some embodiments, the dentifrice composition includes granules.

In some embodiments, the granules may include at least one thickening agent. Examples of suitable thickening agents include, but are not limited to one or more of hydroxypropylmethylcellulose (HPMC), hydroxypropylcellulose (HPC), methylcellulose, and corn starch. In some embodiments, the granules include thickening agents in an amount of 30 to 95 percent by weight. In other embodiments, the granules include thickening agents in an amount of 50 to 85 percent by weight. In one embodiment, the granules include a thickening agent in an amount of 75 percent by weight.

In certain embodiments, the granules include at least one plasticizer. Examples of suitable plasticizers include but are not limited to propylene glycol, glycerin, and triacetin. In some embodiments, the granules include plasticizers in an amount of 5 to 35 percent by weight. In another embodiment, the granules include plasticizers in an amount of 10 to 20 percent by weight.

In certain embodiments, the granules are abrasive. In some embodiments, the granules include a physical abrasive agent. In some embodiments, the physical abrasive agent is silica. In some embodiments, the granules include a physical abrasive agent in an amount of 5 to 50 percent by weight. In some embodiments, the granules include a physical abrasive agent in an amount of 15 to 30 percent by weight.

In some embodiments, granules are present in an amount of 1 to 5 percent by weight of the composition. In some embodiments, the abrasive granule formulations are present in an amount of 1 percent by weight of the dentifrice composition.

The term "orally acceptable vehicle" as used herein shall include a suitable vehicle, which can be used to apply the granules described above to the oral cavity in a safe and effective manner. Such vehicle may include, but is not limited to, materials such as fluoride ion sources, additional anti-calculus agents, buffers, other abrasive materials, peroxide sources, alkali metal bicarbonate salts, thickening materials, humectants, water, surfactants, flavor system, sweetening agents, coloring agents, and mixtures thereof. In certain embodiments, the vehicles may include the usual components of toothpastes, tooth powders, prophylaxis pastes, gels, rinses, lozenges, gums and the like.

In some embodiments, an orally acceptable vehicle includes water.

The orally acceptable vehicle may also include a humectant. In some embodiments, the humectant includes glycerin or sorbitol or an alkylene glycol such as polyethylene glycol or propylene glycol. In some embodiments, the humectant is present in an amount of 15 to 80 percent by weight of the dentifrice composition. In other embodiments, the humectant is present in an amount of 54 to 70 percent by weight.

The orally acceptable vehicle may include an inorganic or a natural or synthetic thickening or gelling agent. In some embodiments, the thickening or gelling agent is present in an amount of 3.5 to 7 percent by weight. In some embodiments, a suitable amount of thickening agent is included in the dentifrice composition to suspend abrasive granules or beads. In some embodiments, a suitable amount of thickening agent is included in the dentifrice composition to form an extrudable, shape-retaining product which can be squeezed from a tube onto a toothbrush and will not fall between the bristles of the brush but rather, will substantially maintain its shape thereon. Suitable thickening or gelling agents for a dentifrice composition may include inorganic thickening silicas (available from Huber Corporation under the trade name designation of Zeodent 165), Irish moss, carrageen, gum tragacanth, and polyvinylpyrrolidone.

In some embodiments, the orally acceptable vehicle includes at least one surfactant. Suitable surfactants may include, but are not limited to, water-soluble salts of higher fatty acid monoglyceride monosulfates, such as the sodium salt of the monosulfated monoglyceride of hydrogenated coconut oil fatty acids, cocamidopropyl betaine, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of suitable amides may include N-lauroyl sarcosine, and the sodium, potassium, and ethanolamine salts of N-lauroyl, N-myristoyl, or N-palmitoyl sarcosine.

In some embodiments, surfactants are present in the dentifrice composition in an amount of 0.1 to 5.0 percent by weight. In other embodiments, surfactants are present in the dentifrice composition in an amount of 0.45 to 2.5 percent by weight. In some embodiments, surfactants are present in the dentifrice composition in an amount of 0.45 to 2.5 percent by weight.

The dentifrice composition may also contain a binding agent. Examples of suitable binding agents may include, but are not limited to, marine colloids, carboxyvinyl polymers, carageenans, starches, water-soluble cellulose ethers such as hydroxyethylcellulose, carboxymethylcellulose (carmellose), hydroxypropyl methyl cellulose and salts thereof (e.g., carmellose sodium), natural gums such as karaya, xanthan, gum arabic and tragacanth, chitosan, colloidal magnesium aluminum silicate, and colloidal silica. In some embodiments, the binding agents are present in an amount of 0.1 to 0.70 percent by weight of the composition.

The dentifrice compositions may also include a flavorant or a mixture of flavorants, including natural or synthetic flavorants, such as flavoring oils, flavoring aldehydes, esters, alcohols, similar materials, and combinations thereof. Examples of suitable flavorants may include vanillin, spearmint oil, cinnamon oil, oil of wintergreen (methylsalicylate), peppermint oil, clove oil, anise oil, eucalyptus oil, citrus oils, fruit oils and essences. In some embodiments, the dentifrice composition includes flavorants such as limonene, menthone, carvone, menthol, anethole, eucalyptus oil, eucalyptol, eugenol, cassia, oxanone, alpha-irisone, propenyl guaiethol, thymol, linalool, benzaldehyde, cinnamaldehyde, N-ethyl-p-menthan-3-carboxamine, N-2,3-trimethyl-2-isopropylbutanamide, 3,1-menthoxypropane-1,2-diol, cinnamaldehyde glycerol acetal (CGA), methone glycerol acetal (MGA) and cineole.

In some embodiments, the dentifrice composition may also include an alpha or beta hydroxyacid. A hydroxyacid may boost the action of naturally occurring enzymes present in the oral cavity. In some embodiments, the dentifrice composition may include a hydroxyacid such as include at least one of lactic acid, glycolic acid, and neutralized salicylic acid. In other embodiments the dentifrice composition may include trypsin and proteases responsible for breaking down the outer cell layers.

In some embodiments, the dentifrice composition includes a hydroxyacid in an amount of 0.05 to 5 wt. %. In other embodiments, the dentifrice composition includes a hydroxyacid in an amount of 0.1 to 1 wt. %.

In some embodiments, the dentifrice composition may also include an abrasive. An abrasive may act as a mechanical and physical means of exfoliation and increased desquamation of the oral mucosa. In some embodiments, the abrasive is distributed throughout an orally acceptable vehicle or it may be present in the granule.

In some embodiments, the dentifrice composition includes silica abrasives. Examples of suitable abrasives include, but are not limited to, silica abrasives such as precipitated silicas, sodium metaphosphate, potassium metaphosphate, tricalcium phosphate, dihydrated dicalcium phosphate, aluminum silicate, calcined alumina, bentonite or other siliceous materials, particulate thermosetting resins, such as melamine, phenolic, and urea-formaldehydes, and cross-linked polyepwddes and polyesters.

An abrasive may be present in any suitable amount. In some embodiments, such abrasives are present in an amount of 1 to 40 percent by weight. In other embodiments, such abrasives are present in an amount of 18 to 20 percent by weight.

In certain embodiments, the dentifrice composition includes abrasive beads. An example of suitable commercially available abrasive beads includes those from Presperse®, such as Microwhite® 50. In some embodiments, abrasive beads have a diameter of 0.1 mm to 5 mm. In certain embodiments, abrasive beads have a diameter of 1 mm to 2 mm. In some embodiments, abrasive beads are present in an amount of 0.1 to 10 percent by weight. In other embodiments, abrasive beads are present in an amount of 0.2 to 3 percent by weight.

Other additives may be included in the dentifrice composition for reasons of manufacturing, stability, aesthetics, therapeutic effect, consumer appeal, etc. Exemplary additives include all other conventional dentifrice additives, viscosity modifiers, diluents, foam modulators, saliva stimulating agents, desensitizing agents, whitening agents, enzymes, pH modifying agents, mouth-feel agents, sweeteners, colorants, opacifiers, and breath freshening agents. Other exemplary agents may include a chlorite ion agent, triclosan, 5-chloro-2-(2,4-dichlorophenoxy)-phenol, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, delmopinol, octapinol, piperidino derivatives, nisin, zinc ion agents, stannous ion agents, essential oils, furanones, cell wall lytic enzymes, lysozyme, plaque matrix inhibitors, dextranases, mutanases, bacteriocins, histatins, defensins, cecropins, augmentin, amoxicillin, tetracycline, doxycycline, minocycline, metronidazole, neomycin, kanamycin, clindamycin, strontium chloride, potassium nitrate, fluoride ion agents, peppermint oil, chlorophyll, lidocaine, benzocaine, amino acids, and peroxides.

In some embodiments, the dentifrice composition is a paste or gel. A suitable amount of thickening agent may be included in the dentifrice composition to suspend the granules or abrasive beads. In some embodiments, a suitable amount of thickening agent is included in the dentifrice composition to form an extrudable, shape-retaining product which can be squeezed from a tube onto a toothbrush and will not fall between the bristles but rather, will substantially maintain its shape thereon.

A dentifrice composition as described above may be applied to an oral cavity soft tissue. In some embodiments, application of the dentifrice composition exfoliates the oral mucosa, including inner cheek, tongue and gingival cells. In some embodiments, the dentifrice composition exfoliates by a mechanical/physical means. In some embodiments, the dentifrice composition exfoliates by chemically changing the rate of oral desquamation. In some embodiments, application of the dentifrice composition reduces the overall bacterial load in saliva and the local bacterial population will be reduced wherever applied or brushed.

In some embodiments, application of the dentifrice composition to an oral cavity provides at least one of the following results: fresh breath due to clinical reduction in volatile sulfur compounds (VSC) produced by oral cavity anaerobic proteolytic bacterial metabolism; antibacterial effects due to a reduction in the whole-mouth bacteria and tongue/inner cheek bacteria; "youthful mouth" due to a decrease in the relative cell age via senescence technique; reduction in inflammation; stimulation of gums resulting in increased blood flow to gums and thus increased saliva flow; decreased formations of bacterial plaques on the posterior part of the tongue; increased ability of the mucosa to "breathe"; improved deposition of other ingredients; increased retention time of deposited actives; and alleviation of morning mouth/breath. The dentifrice compositions may therefore be used in the maintenance of oral health and in the treatment and prevention of oral disease.

In some embodiments, the dentifrice composition may include granules and an alpha or beta hydroxyacid. In some embodiments, the combination of granules and an alpha or beta hydroxyacid synergistically exfoliates and increases desquamation of the oral mucosa.

In some embodiments, the dentifrice composition is a toothpaste and/or gel.

Among embodiments of the invention are systems for exfoliation of the oral cavity soft tissue. The system may include the exfoliating dentifrice composition in any variation as described above, as well as an oral care implement for the application of the dentifrice to the oral cavity soft tissue. For example, the oral care implement may be a tongue cleaner, a toothbrush, a swab, a sponge, a finger cot, a stick, a dental tray, and a strip. The implement may be made of any material known in the art such as, for example, plastic, resin, wood, textile, polymer, sponge, paper, foil, film, metal, and rubber. The oral care implement included in the system may be any known or developed in the art. If desired, one may wish to include an oral care implement that includes a reservoir, cavity or other space in or on which the exfoliating dentifrice may be disposed.

EXPERIMENTAL EXAMPLES

Example 1: Granule Formulations

TABLE 1

Granule Formulations for Exfoliation or Increased Desquamation

| Ingredient | Granule A, wt % | Granule B, wt % | Granule C, wt % |
| --- | --- | --- | --- |
| Average particle size | 1 mm | 0.75 mm | 0.1 mm |
| Hydroxypropyl-methylcellulose | 50 | 35 | 0 |
| Hydroxypropylcellulose (HPC) | 0 | 0 | 60 |

TABLE 1-continued

Granule Formulations for Exfoliation or Increased Desquamation

| Ingredient | Granule A, wt % | Granule B, wt % | Granule C, wt % |
| --- | --- | --- | --- |
| Methylcellulose | 0 | 20 | 0 |
| Corn starch | 0 | 30 | 15 |
| Silica, AC43 | 30 | 0 | 15 |
| Plasticizer, such as propylene glycol, glycerin, triacetin, etc. | 20 | 15 | 10 |
| Total | 100 | 100 | 100 |

Granules were prepared for the following examples according to the above formulas.

Example 2: Dentifrice Composition with 1% Granule A

A dentifrice composition was prepared according to the following formula:

TABLE 2

Sample with 1% Granule A

| Ingredient | Wt % |
| --- | --- |
| Sodium CMC | 0.65 |
| Polyethylene glycol 600 (PEG-12) | 3.0 |
| Sorbitol | 55.441 |
| Sodium saccharin | 0.3 |
| Sodium fluoride | 0.24 |
| Tetrasodium pyrophosphate | 0.5 |
| FD&C Blue #1 dye (1% in water) | 0.4 |
| Silica abrasive (Zeodent 115) | 20 |
| Silica thickener (Zeodent 165) | 4.25 |
| Flavor oil | 1.15 |
| Sodium lauryl sulfate, 100% | 1.5 |
| Cocamidopropyl betaine | 0.45 |
| Granule A | 1.0 |
| Water | Q.S. |

Example 3: Dentifrice Composition with 3% Granule B

A dentifrice composition was prepared according to the following formula:

TABLE 3

Sample with 3% Granule B

| Ingredient | Wt % |
| --- | --- |
| CP purified water | 6 |
| Sodium saccharin | 0.35 |
| Sodium fluoride | 0.243 |
| Glycerin | 20 |
| Propylene glycol | 0.5 |
| Sodium CMC | 1.1 |
| Carrageenan | 0.5 |
| Green dye solution | 0.2 |
| Sorbitol | 20.35 |
| CP purified water | 5.485 |
| Gantrez S-97 Liquid form | 15 |
| NaOH 50% | 1.2 |
| Silica abrasive | 18.5 |
| Silica thickener | 3 |
| Triclosan | 0.3 |
| Flavor | 1.6 |
| SLS, 29.0% | 5.172 |

TABLE 3-continued

| Sample with 3% Granule B | |
|---|---|
| Ingredient | Wt % |
| Neutralized salicylic acid | 0.5 |
| Granule B | 3 |
| Total | 100% |

Example 4: Dentifrice Composition with 5% Granule C

A dentifrice composition was prepared according to the formula in Table 4.

TABLE 4

| Sample with 5% Granule C | |
|---|---|
| Ingredient | Wt % |
| Sodium CMC | 0.65 |
| Polyethylene glycol 600 (PEG-12) | 3.0 |
| Sorbitol | 51.341 |
| Sodium saccharin | 0.3 |
| Sodium fluoride | 0.24 |
| Tetrasodium pyrophosphate | 0.5 |
| FD&C Blue #1 dye (1% in water) | 0.4 |
| Silica abrasive (Zeodent 115) | 20 |
| Silica thickener (Zeodent 165) | 4.25 |
| Flavor oil | 1.15 |
| Sodium lauryl sulfate, 100% | 1.5 |
| Cocamidopropyl betaine | 0.45 |
| Lactic acid | 0.1 |
| Granule C | 5.0 |
| Water | Q.S. |

We claim:

1. An exfoliating dentifrice composition comprising
(A) a plurality of granules, wherein the granules comprise at least one polymeric binding agent;
(B) an orally acceptable vehicle comprising water, wherein at least one of the granules and the orally acceptable vehicle further comprises at least one abrasive agent and having an average particle diameter of 0.01 mm to 4 mm and comprises silica; and
(C) a hydroxyacid,
wherein the granules further comprise a plasticizer selected from the group consisting of propylene glycol, glycerin and triacetin in an amount of 5 to 35 percent by weight of the granule; and
wherein the plurality of granules are present in an amount of 1 to 5 percent by weight of the composition.

2. The dentifrice composition of claim 1 wherein the granules further comprise a thickening agent chosen from hydroxypropylmethylcellulose, hydroxypropylcellulose (HPC), methylcellulose, and corn starch.

3. The dentifrice composition of claim 1, wherein the hydroxyacid is chosen from lactic acid, glycolic acid, and neutralized salicylic acid.

4. The dentifrice of claim 1, further comprising a proteolytic enzyme.

5. The dentifrice of claim 1, further comprising an agent chosen from a chlorite ion agent, triclosan, 5-chloro-2-(2,4-dichlorophenoxy)-phenol, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, delmopinol, octapinol, piperidino derivatives, nisin, zinc ion agents, stannous ion agents, essential oils, furanones, cell wall lytic enzymes, and lysozyme.

6. The dentifrice of claim 1, further comprising an agent chosen from plaque matrix inhibitors, dextranases, mutanases, bacteriocins, histatins, defensins, cecropins, augmentin, amoxicillin, tetracycline, doxycycline, minocycline, metronidazole, neomycin, kanamycin, clindamycin, strontium chloride, potassium nitrate, fluoride ion agents, peppermint oil, chlorophyll, lidocaine, benzocaine, amino acids, and peroxides.

7. A method of exfoliating an oral cavity soft tissue comprising contacting an exfoliating dentifrice composition to an oral cavity soft tissue wherein the dentifrice composition is as defined in claim 1.

8. A system for exfoliation of the soft tissues of the oral cavity comprising: (A) an oral care implement and (B) an exfoliating dentifrice composition according to claim 1.

9. The system of claim 8, wherein the oral care implement is chosen from a tongue cleaner, a toothbrush, a swab, a sponge, a finger cot, a stick, a dental tray, and a strip.

10. The system of claim 8, wherein the oral care implement comprises a reservoir into which the exfoliating dentifrice composition is disposed.

11. The system of claim 8, wherein the oral care implement comprises a material selected from plastic, resin, wood, textile, polymer, sponge, paper, foil, film, metal, and rubber.

* * * * *